United States Patent [19]

Bathelt et al.

[11] Patent Number: 4,709,074

[45] Date of Patent: Nov. 24, 1987

[54] URETHANES CONTAINING PERFLUOROALKYL AND EPICHLOROHYDRIN GROUPS

[75] Inventors: Heinrich Bathelt, Altötting; Winfried Ehrl, Neuötting; Frank Wehowsky, Burgkirchen; Rolf Kleber, Neu-Isenburg; Werner Lotz, Niedernhausen; Wolfgang Glenz, Kelkheim; Hubert Herdt, Langen; Lothar Jäckel, Flörsheim am Main; Jan-Hilbert Mast, Hünfelden; Karl Hintermeier, Frankfurt am Main; Manfred Müller, Gelnhausen, all of Fed. Rep. of Germany

[73] Assignee: Hoechst Aktiengesellschaft, Frankfurt am Main, Fed. Rep. of Germany

[21] Appl. No.: 901,247

[22] Filed: Aug. 28, 1986

[30] Foreign Application Priority Data

Aug. 30, 1985 [DE] Fed. Rep. of Germany ....... 3530967
Feb. 22, 1986 [DE] Fed. Rep. of Germany ....... 3605844

[51] Int. Cl.[4] .......................................... C07C 125/073

[52] U.S. Cl. .................................. 560/33; 8/94.1 R; 8/94.14; 8/115.6; 560/26

[58] Field of Search .................................. 560/26, 33

[56] References Cited

U.S. PATENT DOCUMENTS 4,264,484 4/1981 Patel ............................... 8/115.6 X
4,340,749 7/1982 Patel ................................... 560/182
4,468,527 8/1984 Patel ..................................... 564/96

*Primary Examiner*—Werren B. Lone
*Assistant Examiner*—Vera C. Clarke

[57] ABSTRACT

The novel urethanes correspond to the formula I below

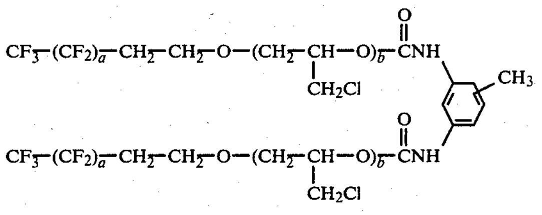

in which a denotes a number from 5 to 17 and b denotes a number from 1 to 7. These urethanes are prepared by reacting the corresponding perfluoroalkylethanol/epichlorohydrin adducts with toluelene diisocyanates. The novel aqueous dispersions are essentially composed of the novel urethanes, cationic or betaine emulsifiers and non-ionic emulsifiers, water-insoluble carboxylic and/or dicarboxylic acid esters and alkanediols or polyalkanediols which can be etherified on one or both sides, in water.

The novel urethanes and the novel aqueous dispersions are used to impart an oleophobic and hydrophobic finish to textiles, leather and furs. They are also suitable for the treatment of unpainted timber, for example unpainted furniture.

3 Claims, No Drawings

URETHANES CONTAINING PERFLUOROALKYL AND EPICHLOROHYDRIN GROUPS

The invention relates to new urethanes containing perfluoroalkyl and epichlorohydrin groups, to aqueous dispersions containing these new urethanes and to the use of these urethanes and dispersions.

U.S. Pat. Nos. 4,264,484, 4,340,749 and 4,468,527 describe urethanes of the formula below, containing perfluoroalkyl and epichlorohydrin groups (cf. formulae I, V and VIII in the said patents),

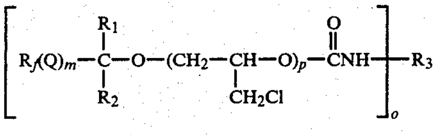

in which $R_f$ denotes a fluoroaliphatic radical,

Q denotes a divalent group which is free from groups capable of epoxy reactions and groups capable of isocyanate reactions, for example a —CO—, —CONR—, —$SO_2$NR, —$SO_2$—, —$C_nH_{2n}$—, —$C_6H_4$—, —$C_6H_3Cl$— or —$OC_2H_4$— group or combinations thereof, in which R is a hydrogen atom or an alkyl radical having 1 to 6 carbon atoms and n is 1 to 20, m denotes 0 or 1, $R_1$ denotes a hydrogen atom or a lower alkyl radical, $R_2$ denotes a hydrogen atom, a lower alkyl radical or an aryl radical having 6 to 12 carbon atoms, or $R_1$ and $R_2$ are linked to one another with the formation of an aromatic or cycloaliphatic structure, p denotes a number having a low value, for example 1 to 5, o denotes a number equivalent to the number of isocyanate groups in the isocyanate, for example 2 to 5, and $R_3$ denotes the isocyanate-free radical of an organic polyisocyanate, such as 2,4-toluylene diisocyanate.

These urethanes are recommended for use as agents for the treatment of textiles.

It has now been found that urethanes of the formula indicated above possess particularly advantageous properties in regard to the treatment of textiles, leather and furs if $R_f$, Q, m, $R_1$, $R_2$, p, o and $R_3$ assume particular meanings or numerical values, that is to say $R_f$ is a selected fluoroaliphatic radical, specifically a linear perfluoroalkyl radical, Q is —$CH_2$—, m is 1, $R_1$ and $R_2$ are H, p is 1 to 7, preferably 1 to 3, o is 2 and $R_3$ is the 2,4-toluylene or 2,6-toluylene diisocyanate radical.

The invention therefore relates to compounds of the formula I below

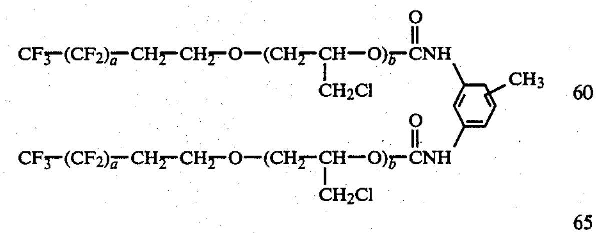

in which a denotes a number from 5 to 17, preferably 7 to 15, and b denotes a number from 1 to 7, preferably 1 to 3.

The preparation of the urethanes according to the invention, i.e. bis-[perfluoroalkylethoxy-(chloromethylethoxy)carbonylamino]-toluenes, is preferably effected by first preparing the perfluoroalkylethanol/epichlorohydrin adduct and reacting this adduct with toluylene diisocyanate. The procedure adopted for the preparation of this perfluoroalkylethanol/epichlorohydrin adduct is preferably to react a perfluoroalkylethanol of the formula II below $$CF_3—(CF_2)_a—CH_2—CH_2—OH,$$

in which a has the abovementioned meaning, or a mixture of such perfluoroalkylethanols, with epichlorohydrin in the presence of Lewis acids as catalysts, at a temperature from 50° to 150° C., preferably from 70° to 90° C. The equation below, in which a and b have the abovementioned meaning, are intended to illustrate this:

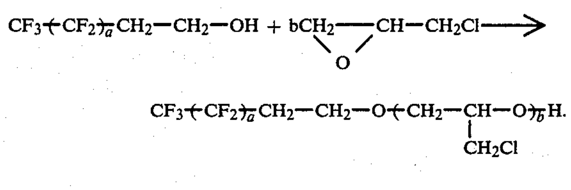

The perfluoroalkylethanols are, as a rule, cheap, commercially available mixtures in which the average value of a is preferably 8 to 12. The nature of the Lewis acid is not critical. $BF_3$, boron trifluoride diethyletherate, $SnCl_4$, $SbCl_5$, $TiCl_4$, $FeCl_3$, $PF_5$ and/or dibutyltin dilaurate are preferred, boron trifluoride diethyletherate being particularly preferred. The amount of catalyst is, in general, 0.01 to 5% by weight, preferably 0.1 to 1% by weight, relative to the perfluoroalkylethanol. The reaction is preferably carried out with stirring and under the autogenous pressure, the liquid epichlorohydrin (boiling point under normal conditions 116° C.) being added to the initially taken alcohol. The duration of the reaction is within the range from about 0.5 to 7 hours. It can be expedient to employ a solvent. Preferred solvents are halogenated hydrocarbons, such as carbon tetrachloride, trichloroethylene, 1,2-dichloroethane, trichloroethane, pentafluoromonochloroethane and trifluorodichloroethane; ketones, such as methyl ethyl ketone and cyclohexanone; ethers, such as diisopropyl ether and tetrahydrofuran; dimethylformamide and N-methylpyrrolidone.

The reaction concerned takes place quantitatively. Any solvent which may have been used is removed from the resulting reaction product by distillation, and any volatile constituents present, such as unreacted epichlorohydrin, are also removed. For reasons of practicality, it is also possible to carry out the distillation in vacuo (water pump vacuum). The Lewis acid employed as catalyst, which does not in itself interfere with the subsequent reaction with toluylene diisocyanate, can be washed out or neutralized by means of alkaline agents, preferably by means of an aqueous solution of sodium bicarbonate or an amine, such as triethylamine.

The procedure adopted for the reaction of the perfluoroalkylethanol/epichlorohydrin adduct with toluylene diisocyanate is preferably initially to take the adduct compound (melting it by heating), to add the toluylene diisocyanate at a temperature from 50° to 150° C., preferably 70° to 120° C., and to allow the reaction to complete itself at the said temperature. This reaction is also carried out with stirring and under the autogenous pressure. The duration of the reaction is within the range from 1 to 15 hours. If it is expedient, the abovementioned solvents can also be employed here. A suitable toluylene diisocyanate is 2,4-toluylene and/or 2,6-toluylene diisocyanate, preferably in the form of a commercial product containing about 80% by weight of 2,4-toluylene diisocyanate and about 20% by weight of 2,6-toluylene diisocyanate. The reaction of the perfluoroalkylethanol/epichlorohydrin adduct with toluylene diisocyanate takes place quantitatively and affords the urethanes according to the invention in the form of solid (waxy) products having the desired degree of purity.

The compounds according to the invention are surprisingly good agents for treating textiles, leather and furs (fur velour) and unpainted timber, particularly textiles, leather and furs. They impart to these articles, above all, an excellent degree of hydrophobic and oleophobic behavior. They also exhibit to an unexpectedly high degree the property of withstanding, without any loss of effect, the severe stresses to which the finished textiles and leather and furs are exposed, for example when they are stretched, texturized, dyed and washed or when subjected to stretching and milling.

The textile material can be of a natural and/or synthetic type. It is preferably composed of polyamide, polyester and/or polyacrylonitrile, polyamide being particularly preferred. The textile material can be in any desired form, for example as filaments, fibers, yarn, flocks, woven fabrics, weftknitted fabrics, warp-knitted fabrics, carpeting or nonwovens. The amount of compound according to the invention applied is so chosen that 0.02 to 1% by weight of fluorine, preferably 0.04 to 0.4% by weight of fluorine, is present on the textile material, calculated from the amount of fluorine in the compound according to the invention; percentages by weight relate to the treated textile material. The nature of the leather and the fur is not critical. The leather can, for example, be cowhide, goat, sheep or pigskin leather and the like. The fur can, for example, be sheepskin velour, mink, raccoon or a similar type of valuable fur. The amount of compound according to the invention to be applied is so chosen that 0.05 to 1.5% by weight of fluorine, preferably 0.1 to 1% of fluorine, are present on the leather or fur, calculated from the amount of fluorine in the compound according to the invention; percentages by weight relate to the treated material (leather or fur).

It has been found that the said effects of the new urethanes of the abovementioned formula I containing perfluoroalkyl and epichlorohydrin groups are achieved above all when they are employed in the form of a specific aqueous dispersion. The aqueous dispersions according to the invention are essentially composed of (A) 5 to 30% by weight, preferably 10 to 25% by weight, percentages by weight relating to the aqueous dispersion, of at least one compound of the formula I as the active compound, (B) 1 to 10% by weight, preferably 3 to 7% by weight, percentages by weight relating to the amount of active compound, of at least one cationic or betaine emulsifier containing at least one perfluoroalkyl radical, (C) 0 to 20% by weight, preferably 5 to 14% by weight, percentages by weight relating to the amount of active compound, of at least one nonionic emulsifier, (D) 50 to 120% by weight, preferably 0 to 110% by weight, percentages by weight relating to the amount of active compound, of at least one water-insoluble carboxylic or dicarboxylic acid ester having 5 to 16 carbon atoms, preferably 6 to 14 carbon atoms, which is liquid at 20° C. and has a boiling point under normal pressure of at least 100° C., (E) 15 to 60% by weight, preferably 20 to 40% by weight, percentages by weight relating to the amount of active compound, of at least one water-soluble alkanediol or polyalkanediol having 2 to 20 carbon atoms, it being possible for the alkanediol and the polyalkanediol to be etherified with 1 or 2 alkyl groups having 1 to 4 carbon atoms, and (F) sufficient water, or water-in-oil emulsion containing at least 50% by weight of water, relative to the emulsion, for 100% by weight of aqueous dispersion to be present.

It is preferable to employ, as the component (A), those compounds of the formula I which are formed when a is a number from 7 to 15 and b is a number from 1 to 3. The compounds below, in which the perfluoroalkyl radical $R_f$ (which corresponds to the radical $CF_3-(CF_2)_a$ of the formula I) is $C_8F_{17}$ to $C_{16}F_{33}$, in particular in the form of the individual compound or in the form of technical mixtures, and b is 1.2 to 2.4, are particularly preferred:

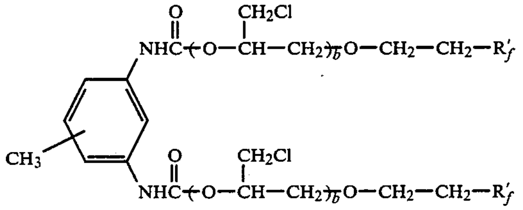

It is preferable to employ, as the component (B), cationic and betaine emulsifiers of the formula

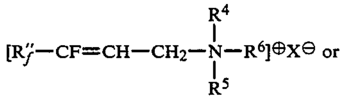

or

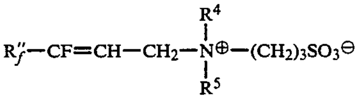

in which $R_f''$ is a perfluoroalkyl radical which has 5 to 13 carbon atoms and can contain a terminal $CF_2H$ group, preferably $C_5F_{11}$, $C_7F_{15}$, $C_9F_{19}$, $C_{11}F_{23}$ and $C_{13}F_{27}$, $R^4$, $R^5$ and $R^6$, which can be identical or different, are an alkyl group which has 1 to 4 carbon atoms and can be substituted by hydroxyl, and X is a monovalent anion, preferably chloride, bromide, sulfate or alkylsulfate having 1 to 2 carbon atoms. The compounds listed below, in which $R_f''$ is $C_5F_{11}$, $C_7F_{15}$, $C_9F_{19}$, $C_{11}F23$ or $C_{13}F_{27}$, constitute particularly preferred cationic emulsifiers:

$[R_f''-CF=CH-CH_2-N(CH_3)_3]^{\oplus}SO_4CH_3^{\ominus}$ $]R_f''-CF=CH-CH_2-N(CH_3)_3]^{\oplus}Cl^{\ominus}$ $[R_f'-CF=CH-CH_2-N(C_2H_5)_2CH_3]^{\oplus}SO_4CH_3^{\ominus}$ $[R_f'-CF=CH-CH_2-N(C_2H_5)_2CH_3]^{\oplus}Cl^{\ominus}$ $[R_f'-CF=CH-CH_2-N(C_3H_7)_2CH_3]^{\oplus}SO_4CH_3^{\ominus}$ $[R_f'-CF=CH-CH_2-N(C_4H_9)_2CH_3]^{\oplus}SO_4CH_3^{\ominus}$ $[R_f'-CF=CH-CH_2-N(CH_3)_2CH_2CH_2OH]^{\oplus}SO_4CH_3^{\ominus}$ $[R_f'-CF=CH-CH_2-N(CH_3)_2CH_2CH_2OH]^{\oplus}Cl^{\ominus}$ $[R_f''-CF=CH-CH_2-\overset{H}{N}H-CH_2-CH_2OH]^{\oplus}Cl^{\ominus}$

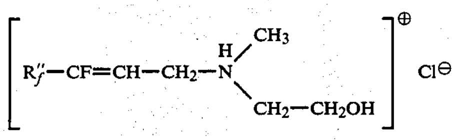

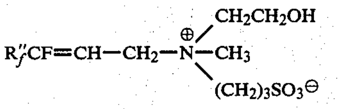

These emulsifiers can be employed as such or dissolved in a solvent; the solvents used are preferably lower alkanols, such as methanol, ethanol, propanol and/or isopropanol, if appropriate together with water. The cationic emulsifiers are preferred.

It is preferable to employ, as the component (C), nonionic emulsifiers of the type of polyoxyethylenesorbitan monooleate or polyoxyethylenesorbitan monostearate having 10 to 30 ethylene oxide units. Polyoxyethylene sorbitan monooleates having 10 to 30 ethylene oxide units are particularly preferred, for example polyoxyethylenesorbitan monooleate having 20 ethylene oxide units, which is known by the trade name Tween 80.

It is preferable to employ, as the component (D), butyl acetate, amyl propionate, methyl butyrate, glycol bisacetate, propanediol bisacetate, diethyl succinate, dimethyl adipate or dibutyl adipate, on their own or mixed with one another. A mixture of a monocarboxylic acid ester, preferably butyl acetate, and a dicarboxylic acid ester, preferably dibutyl adipate, is particularly preferred; the ratio of monocarboxylic acid ester to dicarboxylic acid ester is 1:1 to 1:5, preferably 1:2.

It is preferable to employ, as the Component (E), monoethylene glycol, diethylene glycol, triethylene glycol, tetraethylene glycol, pentaethylene glycol, the corresponding propylene glycols and the ($C_1$-$C_4$)-monoalkyl or -dialkyl ethers of these ethylene glycols and propylene glycols, diethylene glycol dimethyl ether and dipropylene glycol monomethyl ether being particularly preferred.

The compounds corresponding to the components, (B) to (E) are commercially available. They can also be employed in the form of their technical mixtures, which contain, as a rule, several compounds of the type mentioned (mixtures of homologs).

In addition to the components (A) to (F), the aqueous dispersions according to the invention can also contain further suitable components. Thus the dispersion can contain an aliphatic ketone which has a boiling point above 100° C. and is insoluble or sparingly soluble in water; examples thereof are aliphatic ketones having 5 to 8 carbon atoms, such as diethyl ketone, methyl propyl ketone, methyl isobutyl ketone and the like. These ketones are employed in an amount of, preferably, 5 to 10% by weight, percentages by weight relating to the aqueous dispersion, and they can replace a corresponding fraction of component (D).

The aqueous dispersions according to the invention are prepared by mixing the individual components. In this mixing it is preferable to follow a procedure in which the components (A), (B), (C), (D) and (E) are dispersed in water (component F) while a relatively large amount of energy is supplied. The ratios of the components are so chosen that the composition of the dispersion indicated is achieved after dispersion has been carried out. It has proved advantageous to predisperse the component (A) (i.e. the compound according to the invention, the active compound) in at least part of the amount of components (D) and (E) used, and to employ it in this form. It has also proved advantageous to divide the preparation of the aqueous dispersion into two part stages and to carry out first a preliminary dispersion and then a fine dispersion. The preliminary dispersion is expediently carried out by using high shearing forces such as are available when a high-speed stirrer is used, for example a stirrer (dispersing machine) of the Ultraturrax type, and the predispersion thus obtained (crude dispersion) is then expediently subjected to ultrasonic treatment or to treatment in a high-pressure homogenizer. After the completion of this treatment, the particle size in the dispersion is at or below 1 μm to the extent of over 80%, preferably over 95% (fine dispersion).

Finally, the invention relates to the use of the aqueous dispersions described. They are employed in accordance with the invention for treating textiles, leather and fur and unpainted timber (preferably unpainted furniture). They impart an excellent hydrophobic and oleophobic finish to these articles, in particular textiles, leather and fur. When applied to textiles, the aqueous dispersions can be employed in the form in which they are obtained in their preparation. Normally, however, they will be formulated with water to a solids content of 1 to 10% by weight, preferably 1.5 to 5% by weight (percentages by weight relating to the aqueous dispersion), and will be employed in this more dilute form. For treating previously fulled leather and furs, the aqueous dispersions can, if applied as a liquor, be employed directly and without further preliminary dilution in the form in which they are obtained in their preparation. For treating dry leathers and furs by the spray application process, the aqueous dispersions will, however, normally be formulated beforehand with water to a solids content of 1 to 10% by weight, preferably 4 to 8% by weight (percentages by weight relating to the aqueous dispersion), and will be employed in this more dilute form.

The aqueous dispersions according to the invention meet all the requirements of practice and exhibit, in particular, an excellent long-term stability at temperatures from −20° to +40° C. Although they freeze at minus temperatures, the dispersion is preserved after being thawed out. In addition to the excellent oleophobic and hydrophobic properties imparted, a general soil-repellency and also an improvement in conductivity is achieved. The aqueous dispersions described can be employed either on their own for appropriate treatment processes or in combination with, for example, customary spinning preparations or leather fat-liquoring agents or other finishing agents, such as antistatic agents, optical brighteners, textile resins based on glyoxal or derivatives thereof, softeners and dispersion of polyvinyl alcohol and ethylene/vinyl acetate polymers, mineral and synthetic tanning agents and resin and polymeric tanning agents.

What has been said above applies in respect of the nature and form of the textile material employed for the treatment. The textile material can thus be of natural or synthetic type. The aqueous dispersions are particularly advantageously suitable in the case of a textile material composed of polyamide, polyester and/or polyacrylonitrile, especially polyamide. The textile material can be in any desired form; as a rule it will be filaments, fibers, woven fabrics or carpeting. The treatment of textile material with the aqueous dispersions according to the invention is carried out by customary methods, for example by spraying, dipping, slop-padding, padding and the like. The amount applied is so chosen that the amount of fluorine in the active compound (compound according to the invention) on the textile material is 0.02 to 1% by weight, preferably 0.04 to 0.4% by weight, percentages by weight relating to the treated textile material. After the application to the textile material to be treated, drying is carried out at temperatures up to approx. 120° C., for example at 100° to 120° C., and a heat treatment is then carried out at temperatures from approx. 130° to 190° C., preferably 140° to 180° C.; this normally lasts about 30 seconds to about 4 minutes (unless drying and heat treatment are not in any case carried out in the course of preparing the textile material).

As already mentioned above, there are no limitations in respect of the nature and origin of the leather and furs to be finished. Before treatment with the aqueous dispersion, they should, however, as far as possible not be covered with strongly water-repelling agents, such as, for example, a polyurethane dressing, in order to achieve reliable and uniform penetration. The treatment of leather and furs with the aqueous dispersions according to the invention is carried out by the customary methods, for example in a bath, by dipping, brushing or spray application. The amount applied is so chosen that the amount of fluorine in the active compound (compound according to the invention) available for the leather and fur material is 0.05 to 1.5% by weight, preferably 0.1 to 1% by weight, percentages by weight relating to the leather and fur material to be treated. After being treated with the aqueous dispersion according to the invention, the leather and fur material can be dried and finished in the customary manner. The treatment with the aqueous dispersion according to the invention does not impair either the color or the handle of the treated leather and furs, nor is the free movement of the wool and hairs of furs impaired by the latter becoming glued.

The invention will now be illustrated in greater detail by means of examples.

Compounds according to the invention

1. Preparation of the perfluoroalkylethanol/epichlorohydrin adducts

EXAMPLE 1

1.5 kg (2.78 mol) of a commercially available mixture of perfluoroalkylethanols (perfluoroalkyl=$C_6F_{13}$ to $C_{14}F_{29}$; OH number=104), 450 ml of 1,2,2-trifluorotrichloroethane ($CFCl_2-CF_2Cl$; b.p.=48° C.) as solvent and 15 g of boron trifluoride diethyletherate as catalyst (i.e. 1% by weight of catalyst, relative to perfluoroalkylethanol) were initially placed in a 2 liter flask equipped with a stirrer, a reflux condenser, a thermometer, a dropping funnel and a heating bath. 309 g (3.34 mol) of epichlorohydrin were added dropwise to this solution at 50° C. (with cooling), after which stirring was continued for a further 2 hours at the boiling point of the solvent. The contents of the flask were then washed with 1 liter of 4% strength by weight aqueous sodium bicarbonate solution in order to remove the catalyst, then washed again twice with water and distilled in vacuo (water pump vacuum) in order to remove the solvent.

The perfluoroalkylethanol/epichlorohydrin adduct obtained (1.77 kg; yield: 97.6% by weight of theory) was a solid (waxy), yellow product (OH number 85.9); its overall composition corresponds to the formula (molar ratio of perfluoroalkylethanol to epichlorohydrin=1:1.2):

$$(C_6F_{13}-C_{14}F_{29})-CH_2CH_2O-(CH_2-\underset{\displaystyle CH_2Cl}{\underset{|}{C}}HO)_{1,2}-H.$$

EXAMPLE 2

150 g (0.28 mol) of a commercially available mixture of perfluoroalkylethanols (perfluoroalkyl=$C_8F_{17}$ to $C_{16}F_{33}$; OH number=105.4) were melted by heating to 70° C. in a 250 ml flask equipped with a stirrer, a reflux condenser, a thermometer, a dropping funnel and a heating bath, and 1.3 g of boron trifluoride diethyletherate were added as catalyst, after which 36.5 g (0.40 mol) of epichlorohydrin were metered in at a temperature of 70° to 90° C. The mixture was then allowed to react for a further 3 hours at 75° C. 0.9 g of triethylamine was added to the contents of the flask in order to neutralize the catalyst, and the mixture was then subjected to incipient distillation at 75° C. and 15 mbar in order to remove volatile constituents. A solid (waxy), yellow product (186.8 g; yield: 99.4% by weight of theory; OH number=79.7) was obtained. Its overall composition corresponds to the formula (molar ratio of perfluoroalkylethanol to epichlorohydrin=1:1.4):

$$(C_8F_{17}-C_{16}F_{33})-CH_2CH_2O-(CH_2\underset{\displaystyle CH_2Cl}{\underset{|}{C}}HO)_{1,4}-H.$$

EXAMPLES 3 TO 6

The procedure followed was in each case analogous to that of Example 2, the perfluoroalkylethanol and the epichlorohydrin being employed in the molar ratios listed below. The table also contains the yield and the OH number of the perfluoroalkylethanol/epichlorohydrin adducts obtained.

| | Molar ratio of perfluoro-alkylethanol to epichloro-hydrin | Yield (% by weight) | OH number |
|---|---|---|---|
| Example 3 | 1:1.6 | 99.0 | 78.1 |
| Example 4 | 1:1.8 | 99.1 | 76.3 |
| Example 5 | 1:2.0 | 98.7 | 75.4 |
| Example 6 | 1:2.4 | 99.2 | 72.2 |

The overall compositions of the compounds obtained in accordance with Examples 3 to 6 correspond to the formula of the compound of Example 2, with the exception that the indices 1.6, 1.8, 2.0 and 2.4, respectively, replace the index 1.4.

2. Preparation of the diurethane compounds according to the invention

EXAMPLE 7

548.5 g (0.84 mol) of perfluoroalkylethanol/epichlorohydrin adduct from Example 1, melted at 80° C., were initially placed in a 1 liter flask equipped with a stirrer, a condenser containing a drying tube, a thermometer and a heating bath. 73.1 g (0.42 mol) of toluylene diisocyanate, specifically a mixture of 80% by weight of 2,4-toluylene diisocyanate and 20% by weight 2,6-toluylene diisocyanate (a commercial product), were then added dropwise, after which the mixture was stirred for a further 5 hours at 110° C. The diurethane compound obtained (614 g; yield: 98.8% by weight of theory) was a solid (waxy), yellow product having a fluorine content of 51.4% by weight. Its overall composition corresponds to the formula

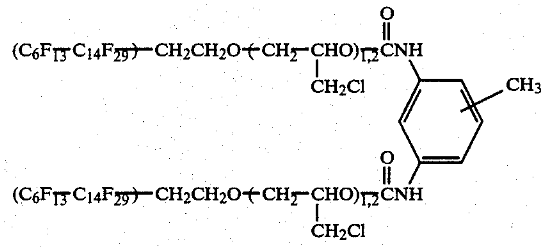

EXAMPLES 8 TO 12

The procedure followed was in each case analogous to that of Example 7, the perfluoroalkylethanol/epichlorohydrin adducts of Examples 2 to 6 being reacted with toluylene diisocyanate in a molar ratio of 2:1. The yields and the fluorine contents of each of the compounds obtained are listed below:

| | Perfluoroalkylethanol/ epichlorohydrin adduct from Example | Yield (% by weight) | Fluorine content (% by weight) |
|---|---|---|---|
| Example 8 | 2 | 97.3 | 50.3 |
| Example 9 | 3 | 98.5 | 49.3 |
| Example 10 | 4 | 99.1 | 48.1 |
| Example 11 | 5 | 97.7 | 47.0 |
| Example 12 | 6 | 99.6 | 46.0 |

The overall composition of the compounds, according to the invention, obtained in accordance with Examples 8 to 12 corresponds to the formula of the compound of Example 7, with the exception that the radical $C_8F_{17}$—$C_{16}F_{33}$ replaces the radical $C_6F_{13}$—$C_{14}F_{29}$, and the indices 1.4, 1.6, 1.8, 2.0 and 2.4, respectively, replace the index 1.2.

Aqueous dispersions according to the invention

EXAMPLE 13

10 kg of aqueous dispersion according to the invention were prepared by mixing the components (A) to (F) listed below:

(A) 1.74 kg of compound according to the invention (active substance) according to Example 10, (B) 0.10 kg of cationic emulsifier (in 0.14 kg of isopropanol and 0.02 kg of water as solvents) of the formular below $$[C_9F_{19}—CF{=}CH—CH_2—N(C_2H_5)_2CH_3]\text{-}^{\oplus}SO_4CH_3^{\ominus}$$

(C) 0.20 kg of polyoxyethylenesorbitan monooleate containing 20 oxyethylene units (commercial product Tween 80) as a nonionic emulsifier, (D) 1.50 kg composed of 1.0 kg of dibutyl adipate and 0.5 kg of butyl acetate, (E) 0.50 kg of diethylene glycol dimethyl ether, and (F) 5.80 kg of water.

The sum of (A) to (F) plus solvent for the component (B) is 10.00 kg.

If the amount of active substance and the amount of water are related to the aqueous dispersion, and the amount of the components (B) to (E) is related in each case to the active substance, the percentages by weight listed below are obtained for the components (A) to (F):

(A) 17.4% by weight
(B) 5.7% by weight
(C) 11.5% by weight
(D) 86.2% by weight
(E) 28.7% by weight
(F) 58.0% by weight.

The detailed preparation of the dispersion according to the invention was effected as follows:

5.8 kg of water (component F) and 0.25 kg of a 40% strength by weight solution of the cationic emulsifier (component B) in 90% strength aqueous isopropanol were stirred in a 20 liter broad cylindrical vessel (hence 0.1 kg of cationic emulsifier and 0.16 kg of solvent composed of 0.14 kg of propanol and 0.02 kg of water were thus introduced). A solution, at 80° C., of 1.74 kg of active substance (component A) in 0.2 kg of polyoxyethylenesorbitan monooleate containing 20 oxyethylene units (component C), 1.0 kg of dibutyl adipate and 0.5 kg of butyl acetate (component D) and 0.5 kg of diethylene glycol dimethyl ether (component E) were stirred into the above mixture at room temperature under the strong shearing action of a dispersing machine of the Ultraturrax type, in the course of which the temperature in the vessel rose to 35° C. The coarse dispersion was subjected to treatment with the Ultraturrax for approx. 30 minutes, in the course of which the temperature rose to 40° to 45° C. A superficially attractive emulsion was already formed in this way, but it is not yet stable on storage in this form and would soon settle out. The crude dispersion obtained was then subjected to a final fine dispersion, specifically by sonic irradiation by means of an ultrasonic machine (for example the sonifier model made by Branson), until at least 90% of the particles had reached an average size of 1 μm or less. In order to achieve the best efficiency of the ultrasonic machine and optimum sonic irradiation, it is best to pump the crude dispersion through the reverberation chamber, controlled at a temperature of 40° C. (the temperature control of the reverberation chamber is achieved by means of a water bath controlled by a thermostat) until the required fine dispersion has been reached, for which a second and third pass may in some cases be necessary; flow rate 10 liters/hour.

This gives 10 kg of a very fine, milky, opaque dispersion containing 8% by weight of active fluorine (calculated from the amount of active substance in the dispersion), and this dispersion is also satisfactorily stable on storage at −20° C. and +40° C.

EXAMPLE 14

The procedure followed was as in Example 13, 1.51 kg of compound according to the invention (active substance) according to Example 7 being employed as the component A. As in Example 13, the mixture was formulated to 10 kg of aqueous dispersion, using an appropriate amount of water. This gave an excellent, stable dispersion containing 8% of active fluorine. The dispersion is composed, accordingly, of: (A) 1.51 kg; (B) 1.10 kg with a total of 0.16 kg of solvent; (C) 0.20 kg; (D) 1.50 kg; (E) 0.50 kg; and (F) 6.03 kg.

If the amount of active substance and the amount of water are related to the aqueous dispersion and the amounts of the components (B) to (E) are each related to the active substance, the percentages by weight listed below are obtained for the components (A) to (F):

(A) 15.1% by weight
(B) 6.6% by weight
(C) 13.2% by weight
(D) 100.0% by weight
(E) 33.1% by weight
(F) 60.3% by weight

EXAMPLE 15

The procedure followed was as in Example 13, 1.76 kg of compound according to the invention (active substance) according to Example 11 being employed as the component (A). As in Example 13, a mixture was formulated to give 10 kg of aqueous dispersion, using an appropriate amount of water. This gave an excellent, stable dispersion containing 8% by weight of active fluorine. Because of the small difference between 1.74 kg of active component in Example 13 and the 1.76 kg in this example, the amounts of components (A) to (F) as percentages by weight relative to the active substance or to the aqueous dispersion are virtually the same as the corresponding amounts in Example 13.

EXAMPLE 16

The procedure followed was as in Example 13, 1.77 kg of compound according to the invention (active substance) according to Example 12 being employed as the component (A). As in Example 13, 10 kg of an excellent, stable aqueous dispersion containing 8% by weight of active fluorine were obtained. The statement at the end of Example 15 in regard to the amounts of the components (A) to (F) in percent by weight, relative to active substance or to aqueous dispersion, also applies in this example.

Examples of use with textiles

EXAMPLES 17 TO 20

The compounds, according to the invention of Examples 8 to 11 were tested. The compounds were applied to a woven fabric composed of polyamide 6 filaments by means of a padder, at a liquor pick-up of 30 to 40% by weight. The amount of compound according to the invention (active substance) in each liquor was so chosen that in each case the amount applied was approx. 0.05% by weight of fluorine (active fluorine) on the woven fabric after the condensation (percentages relating to the weight of the fabric). The liquor was composed of approx. 1.2 g of compound according to the invention in 250 ml of acetone (acetone liquor). The acetone-moist fabric was first dried in air and then subjected to condensation (fixed) for 1 minute at 160° C.

The oil-repellency values of the fabrics thus obtained were determined as specified in AATCC Test Standard 118-1978, specifically after the condensation and after 3 hours treatment by washing at the boil with an alkaline liquor composed of 1 liter of water, 1 g of trisodium phosphate and 2 g of a fatty acid polyglycol ester obtained by oxyethylating 1,4-butanediol with 15 mol of ethylene oxide and subsequently esterifying the oxyethylate with 1 mol of oleic acid. The fluorine applied (F applied in % by weight, relative to the weight of the fabric) was also determined after condensation and after the alkaline wash at the boil. The results are listed in the table below:

| Compound from Examples | Oil-repellency after condensation | Oil repellency after washing at the boil | F applied after condensation (% by weight) | F applied after washing at the boil (% by weight) | F retention (% by weight) |
|---|---|---|---|---|---|
| 8 | 4-5 | 4 | 0.056 | 0.028 | 50 |
| 9 | 4-5 | 4 | 0.055 | 0.031 | 56 |
| 10 | 5 | 5 | 0.060 | 0.027 | 45 |
| 11 | 5 | 3-4 | 0.060 | 0.023 | 39 |

EXAMPLES 21 TO 24

The aqueous dispersions, according to the invention, of Examples 13 to 16 were tested. The dispersions were diluted with water to a solids content of 2 to 4% by weight. The diluted dispersions (liquors) were applied to a woven fabric composed of polyamide 6 filaments by means of a padder and at a liquor pick-up of 30 to 40% by weight, so that in each case the amount applied was approx. 0.05% by weight of fluorine (active fluorine) on the fabric after the condensation (percentages by weight relating to the weight of the fabric). The fabrics, moist with liquor, were first dried at temperatures up to 120° C. and were then subjected to condensation at 200° C. for 3 minutes. The oil-repellency values of the fabrics thus obtained were determined as specified in AATCC Test Standard 118-1978, specifically after the condensation and after 3 hours treatment with the alkaline boiling wash liquor mentioned above. The fluorine applied (F applied in % by weight, relative to the weight of the fabric) was also determined after the condensation and after the alkaline boiling wash. The results are listed in the table below:

| Aqueous dispersion from examples | Oil repellency after condensation | Oil repellency after washing at the boil | F applied after condensation (% by weight) | F applied after washing at the boil (% by weight) | F retention (% by weight) |
|---|---|---|---|---|---|
| 13 | 5 | 5 | 0.051 | 0.025 | 49 |
| 14 | 5 | 3 | 0.049 | 0.021 | 43 |
| 15 | 5 | 3 | 0.048 | 0.020 | 42 |
| 16 | 5 | 5 | 0.050 | 0.023 | 46 |

COMPARISON EXAMPLE

The U.S. patents mentioned initially specifically recommend urethanes which contain perfluoroalkyl and epichlorohydrin groups and, in contrast with the urethanes according to the invention, contain an $-SO_2NR-$ group (cf. the examples of the U.S. patents). The compound below

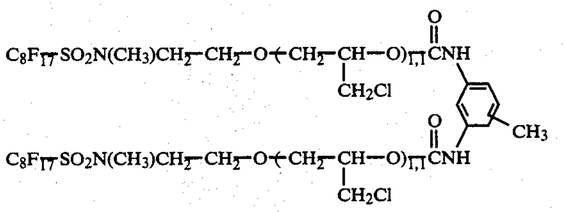

described in Example 4 of the U.S. patents was tested in this comparison example.

The procedure followed was as in Examples 17 to 20. The oil-repellency values after the condensation and after 3 hours treatment with the alkaline boiling wash liquor were determined, as in Examples 17 to 20, on the fabric obtained after treatment with the acetone liquor and the condensation reaction at 160° C. The fluorine applied (F applied in % by weight, relative to the weight of the fabric) was also determined after the condensation and after the alkaline boiling wash. The results are listed below:

| Oil-repellency after condensation | Oil repellency after washing at the boil | F applied after condensation (% by weight) | F applied after washing at the boil (% by weight) | F retention (% by weight) |
|---|---|---|---|---|
| 5 | 1 | 0.092 | 0.065 | 71 |

As the results show, appreciably higher oil-repellency values after the boiling wash are achieved using the compounds according to the invention, that is to say the compounds according to the invention also possess, inter alia, the particularly important property of withstanding the extremely severe stresses in the boiling wash.

Examples of use with leather and furs

EXAMPLES 25 TO 28

The compounds, according to the invention, of Examples 8 to 11 were tested. The compounds were applied to non-finished leather by spray application. The amount of compound according to the invention (active substance) applied in each case was so chosen that approx. 0.5 to 0.6 g of fluorine were applied per $m^2$ of leather surface. Application was effected in each case using a 0.5% strength by weight acetone solution of active substance. After the solvent had evaporated and the leather thus treated had been stored for one day, the water-repellent effect was determined by means of the water spotting test (measurement of the time elapsed before an applied drop of water of definite size had been absorbed by the leather).

Whereas on untreated leather the drop of water applied was absorbed after 2 to 5 minutes, on leather finished with the compounds, according to the invention, of Examples 8 to 11 dwell times of more than 1 hour, as a rule 2 to 3 hours, were observed before the drops of water applied had been absorbed.

EXAMPLES 29 TO 32

The aqueous dispersions, according to the invention, of Examples 13 to 16 were tested. The dispersions were applied to non-finished leather both by the spray process and by the bath process. For application by the spray technique, the aqueous dispersions according to the invention were diluted with water to solids contents of 4 to 8% by weight. In each case approx. 1.6 g of fluorine/$m^2$ of leather were applied by means of a spray gun. After drying, milling or brushing, the water-repellent effect was tested by the water spotting test, and the oil-repellent effect was tested by AATCC Test 118. Whereas a non-finished comparison sample reached dwell times in the water spotting test of less than 5 minutes and an oil-repellency value of only 1 in the AATCC test, the samples of leather finished with the aqueous dispersions according to the invention achieved dwell times in the water spotting test of over 8 hours and oil-repellency values of 5 or more.

For finishing leather in a bath, the aqueous dispersions according to the invention were added, undiluted in an amount of 0.3% by weight of fluorine, relative to shaved weight of leather, to the fat-liquoring bath (which contained a liquor amounting to 150% by weight of water, relative to shaved weight of leather-)—using the customary process of leather production by chrome tanning, re-tanning, dyeing and fat-liquoring. After the leather samples had been dried and finished in the customary manner, the water-repellent effect was tested by the water spotting test, and the oil-repelling action was tested by the AATCC test mentioned. A water-spotting test on the leather samples thus treated gave dwell times of over 8 hours until the water drops applied had been absorbed, and oil-repellency values of 5 or more were reached.

As the results of the use examples show, the compounds and aqueous dispersions according to the invention constitute excellent finishing agents for leather and furs.

We claim:

1. A urethane containing perfluoroalkyl and epichlorohydrin groups, of formula I below

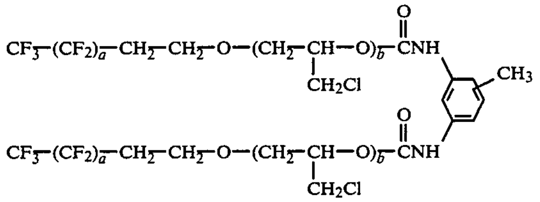

in which a denotes a number from 5 to 17 and b denotes a number from 1 to 7.

2. A urethane as claimed in claim 1, wherein a is 7 to 15 and b is 1 to 3.

3. A urethane as claimed in claim 1, wherein a ranges from 7 to 15, so that $CF_3$—$(CF_2)_a$— is perfluoroalkyl of the formula $C_8F_{17}$— to $C_{16}F_{33}$—.

* * * * *

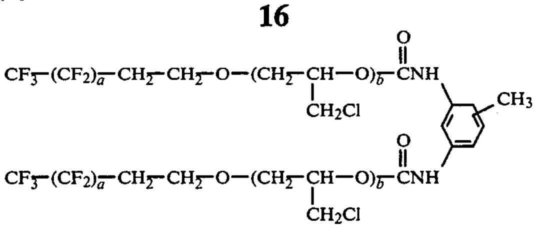

in which a denotes a number from 5 to 17 and b denotes a number from 1 to 7.

2. A urethane as claimed in claim 1, wherein a is 7 to 15 and b is 1 to 3.

3. A urethane as claimed in claim 1, wherein a ranges from 7 to 15, so that $CF_3$—$(CF_2)_a$— is perfluoroalkyl of the formula $C_8F_{17}$— to $C_{16}F_{33}$—.

* * * * *